United States Patent
Streckfus et al.

(10) Patent No.: US 8,772,038 B2
(45) Date of Patent: Jul. 8, 2014

(54) DETECTION OF SALIVA PROTEINS MODULATED SECONDARY TO DUCTAL CARCINOMA IN SITU OF THE BREAST

(71) Applicant: Board of Regents of the University of Texas System, Austin, TX (US)

(72) Inventors: Charles F. Streckfus, Houston, TX (US); William P. Dubinsky, Houston, TX (US); Lenora R. Bigler, Houston, TX (US)

(73) Assignee: Board of Regents of the University of Texas System, Houston, TX (US)

( * ) Notice: Subject to any disclaimer, the term of this patent is extended or adjusted under 35 U.S.C. 154(b) by 0 days.

(21) Appl. No.: 13/918,467

(22) Filed: Jun. 14, 2013

(65) Prior Publication Data

US 2013/0280743 A1 Oct. 24, 2013

Related U.S. Application Data

(63) Continuation of application No. 12/678,686, filed as application No. PCT/US2008/075955 on Sep. 11, 2008, now abandoned.

(60) Provisional application No. 60/973,372, filed on Sep. 18, 2007.

(51) Int. Cl.
*G01N 33/68* (2006.01)
*G01N 33/48* (2006.01)
*G01N 27/62* (2006.01)
*G01N 33/574* (2006.01)

(52) U.S. Cl.
CPC ............ *G01N 27/62* (2013.01); *G01N 2800/60* (2013.01); *G01N 2800/50* (2013.01); *G01N 33/57415* (2013.01)
USPC .................. 436/64; 436/63; 436/86; 436/161; 436/173

(58) Field of Classification Search
USPC ........... 436/63, 64, 86, 56, 161, 173; 435/7.1, 435/7.21, 7.23
See application file for complete search history.

(56) References Cited

U.S. PATENT DOCUMENTS

| 6,294,349 B1 | 9/2001 | Streckfus et al. |
| 6,972,180 B1 | 12/2005 | Streckfus et al. |
| 7,811,774 B2 | 10/2010 | Ring et al. |
| 7,951,529 B2 | 5/2011 | Li et al. |
| 2004/0033613 A1 | 2/2004 | Zwick et al. |
| 2006/0063269 A1 | 3/2006 | Agnew et al. |
| 2007/0111244 A1 | 5/2007 | Georges et al. |

FOREIGN PATENT DOCUMENTS

WO 0052469 A1 9/2000

OTHER PUBLICATIONS

EP Application No. EP 08832313, Supplementary Search Report Dated Feb. 11, 2011, 11 pages.
Bigler, Lenora et al., "Salivary Biomarkers for the Detection of Malignant Tumors That Are Remote From the Oral Cavity," Clinics in Laboratory Medicine, W.B. Saunders, Co., London, GB, vol. 29, No. 1, Mar. 1, 2009, pp. 71-85, XP009142585.
Streckfus, C. et al., "A Preliminary Study of CA15-3, C-ERB-2, Epidermal Growth Factor Receptor, Cathepsin-D, and P53 in Saliva Among Women With Breast Carcinoma," Cancer Investigation, vol. 18, No. 2, Jan. 1, 2000, pp. 101-109, XP002942881.
Streckfus, C. et al., "Using LC-MS/MS Mass Spectrometry to Identify Breast Cancer Biomarkers in Saliva," Oral Surgery, Oral Medicine, Oral Pathology, Oral Radiology and Endodontology, vol. 102, No. 3, Sep. 1, 2006, pp. 337-338, XP005603545.
Streckfus, C. et al., "A Comparison of the Proteomic Expression in Pooled Saliva Specimens From Indviduals Diagnosed With Ductal Carcinoma of the Breast With and Without Lymph Node Involvement," Journal of Oncology, vol. 2009, pp. 1-11, XP002616034.
Streckfus et al. Cancer Investigation, vol. 26, Mar. 2008, pp. 159-167.

*Primary Examiner* — Maureen Wallenhorst
(74) *Attorney, Agent, or Firm* — Conley Rose, P.C.

(57) ABSTRACT

A method of differentiating among the presence of ductal carcinoma in situ in the breast, benign fibroadenoma of the breast, and non-cancerous breast tissue in a subject is disclosed. The method involves measuring the concentration of at least one protein biomarker selected from a group of forty-nine differentially expressed proteins in the saliva of persons with DCIS, or benign fibroadenoma, or in persons who are cancer-free. The resulting test data is compared to a reference panel. From the comparison the presence in the subject of either ductal carcinoma in situ of the breast, or benign fibroadenoma of the breast is determined.

13 Claims, 4 Drawing Sheets

FIG. 1

Key:

1 = Cell Adhesion & Communication Proteins
2 = Cytoskeleton Associated Proteins
3 = Energy Metabolism Proteins
4 = Immune Response Proteins
5 = Inhibitors of Cysteine Proteases
6 = Indicators of Tissue Damage
7 = Inhibitors of G1 CDK's, Modulaters of NK Activity
8 = Calcium Binding Protein
9 = Membrane Associated Protein
10 = Protein with Binding Functions
11 = Protein Degradation & Inhibitor
12 = Signaling Proteins
13 = Surface Antigens (growth)
14 = Proteins involved with Transport

DETECTION OF SALIVA PROTEINS MODULATED SECONDARY TO DUCTAL CARCINOMA IN SITU OF THE BREAST

CROSS-REFERENCE TO RELATED APPLICATIONS

This non provisional application is a continuation of application Ser. No. 12/678,686, filed on Jun. 29, 2010, now abandoned, which is a 371 of PCT/US2008/075955, filed on Sep. 11, 2008, which claims priority to U.S. provisional application Ser. No. 60/973,372, filed on Sep. 18, 2007.

BACKGROUND

1. Technical Field

The invention generally relates to methods and compositions for diagnosing breast cancer, and, more particularly, to such methods and compositions which use the differential expression of protein biomarkers in the saliva of an individual to differentiate among ductal carcinoma in situ of the breast, benign fibroadenoma and non-cancerous tissue in that individual.

2. Description of Related Art

Conventional physical examination and mammography are useful screening procedures for the early detection of breast cancer. However, they can produce a substantial percentage of false positive and false negative results especially in women with dense parenchymal breast tissue. Consequently, screening results in a number of negative biopsy results yielding a high percentage of false positives. There is also a demonstrated lack of sensitivity in detecting cancerous lesions in younger women yielding a significant percentage of false negatives. Although advanced technology in the field of mammography allows more reliable detection of small lesions of the breast, a clear need exists for added modalities of screening, particularly for diagnosing cancer in younger women.

There has been extensive use of immunohistochemistry to detect expression of specific biomarkers as a potential adjunct diagnostic procedure for certain tumors. Primarily, the markers have been found in serum and in tissues. Protein tumor markers such as c-erbB-2 (erb) and Cathespin-D (CD) have been assayed in tissue and shown to correlate with aggressive lesions.

The term "proteomics" was originally defined to represent the analysis of the entire protein component of a cell or tissue, but that term now encompasses the study of expressed proteins, including identification and elucidation of the structure-function relationship under healthy conditions and disease conditions. In combination with genomics, proteomics can provide a holistic understanding of the biology underlying disease processes. Information at the level of the proteome is critical for understanding the function of specific cell types and their role in health and disease (1, 2).

Protein expression and function are subject to modulation through transcription as well as through posttranscriptional and translational events. Multiple RNA species can result from one gene through a process of differential splicing. Additionally, there are more than 200 post-translation modifications that proteins could undergo that affect function, protein-protein and nuclide-protein interaction, stability, targeting half-life, and so on (6), all contributing to a potentially large number of protein products from one gene. Identifying and understanding these changes are the underlying themes in proteomics (6-9).

Technological advancements have benefited proteomic research to the point where saliva is now being assayed for protein content using the latest available proteomic technology (10). There is a paucity of information regarding the salivary proteome and its constituents in the presence of disease such as carcinoma. One inventor's previous studies using immunological techniques have demonstrated that saliva from breast cancer patients exhibited elevated levels of c-erbB-2, CA 15-3, EGFR, cathepsin D and p53, suggesting that there is communication between the breast tumor and the salivary gland (11, 12). In single analyte reports, additional low-abundance proteins such as HER2/neu, Waf-1, pantropic p53, EGFR and cathepsin D were found to be altered (12). Recently, the tumor biomarkers CA 125, c-erB-2 (erb) and Cathespin-D (CD) have been detected in saliva and employed in a diagnostic panel for the initial detection and follow-up screening of breast cancer patients. There is continuing interest in the development of adjunct diagnostic procedures to enhance breast cancer screening.

BRIEF SUMMARY

In accordance with certain embodiments of the invention, a method of diagnosing the likelihood of the presence or occurrence of breast tumor in a test subject is provided. The method comprises (a) measuring in a saliva sample from the test subject the concentration of at least a first protein biomarker, wherein each biomarker is known to be differentially expressed in breast tumor and tumor-free breast tissue, wherein the breast tumor comprises benign fibroadenoma or ductal carcinoma in situ of the breast (DCIS), to provide a set of test data comprising a concentration value of each said protein biomarker in the saliva sample. The term "concentration value" may be a quantitative amount or any other appropriate indication of a concentration, such as, for example, a colorimetric indicator score (e.g., +/−). The method further includes (b) comparing the test values to a reference panel comprising (1) a mean concentration value of each said protein in saliva from a group of breast tumor-free individuals (reference control group), (2) a mean concentration value of each said protein in saliva from a group of individuals with DCIS (reference DCIS group), or from a group of individuals with benign fibroadenoma of the breast (reference benign group), or from both the DCIS group and the benign group; and (c) determining from that comparison a diagnosis of likelihood of the presence or occurrence of a breast tumor in the test subject. In some embodiments the mean concentration ranges include a tolerance range or statistical error range.

In some embodiments, in (a), at least the first biomarker is known to be differentially expressed among benign fibroadenoma, DCIS and tumor-free breast tissue; in (b), step (2) comprises: (2') a mean concentration value of each said protein in saliva from the reference DCIS group, and (2") a mean concentration value of each said protein in saliva from the benign group in the reference panel, and in (c), the previously described step of "determining" comprises determining from the comparison a diagnosis of likelihood of the presence or occurrence of either DCIS or fibroadenoma of the breast in the test subject.

In some embodiments, the concentration value of at least the first protein biomarker in the reference panel is significantly different in the saliva of the DCIS group in the reference panel and/or in the saliva of the benign group in the reference panel, relative to the respective level of each said protein biomarker in the saliva of the control group in the reference panel. In certain embodiments, the concentration value difference of at least the first protein biomarker is significant at a level in the range of p<0.05 to p<0.0001. In some embodiments, the concentration value difference of the first protein biomarker is significant at a level in the range of p<0.001 to p<0001.

In some embodiments, at least the first protein biomarker is selected from the group consisting of CAH6, K2C4, CYTA, FABP4, IGHGI, TRFL, BPIL1, CYTC, HPT, PROF1 and ZA2G, and, in (c), the above mentioned step of "determining" comprises determining from the comparison a diagnosis of likelihood of the presence or occurrence of DCIS in the test subject.

In some embodiments, at least the first protein biomarker is selected from the group consisting of ENOA, IGHA2, IL-1 ra, S10A7, SPLC2, and, in (c), the "determining" step comprises determining from the comparison a diagnosis of likelihood of the presence or occurrence of fibroadenoma in the test subject.

In some embodiments, the reference panel is prepared by analyzing salivary proteins by isotopic labeling and liquid chromatography tandem mass spectrometry to characterize salivary proteins from each said group, and determining from the above-mentioned analysis the differential concentrations of the protein biomarkers in individuals with ductal carcinoma in situ of the breast, in individuals with benign fibroadenoma of the breast, and in individuals free of both ductal carcinoma in situ and benign fibroadenoma.

In some embodiments, in step (a), "measuring" comprises analyzing the salivary protein-containing sample by isotopic labeling and liquid chromatography tandem mass spectrometry to characterize the protein biomarkers. In some embodiments, the isotopic labeling comprises differential isotopic labeling of salivary proteins of at least first and second saliva samples.

In some embodiments, in step (b), the "comparing" step yields a comparison result in which the concentration value of at least a first protein biomarker is a greater than 50% change relative to the mean concentration value of the respective protein in the control group of the reference panel.

In some embodiments, a first saliva sample is obtained from the test subject, and, in (a), the set of test data is a first set of test data. In this case, the method further comprises: (d) obtaining a second saliva sample from the test subject subsequent to the first saliva sample; (e) measuring the concentration of at least the first protein biomarker in the second saliva sample, to provide a second set of test data comprising a second concentration value of each protein biomarker in the saliva sample; (f) comparing the second set of test data to the reference panel; and (g) determining from the result of that comparison a diagnosis of likelihood of the presence or occurrence of either DCIS or benign fibroadenoma of the breast in the test subject.

In some embodiments, the method further includes (h) comparing the second set of test data to the first set of test data to determine whether a difference in the concentration value of at least the first protein biomarker exists between the first and second sets of test data for the test subject. In some embodiments, the first saliva sample is obtained prior to surgical removal of cancerous breast tissue from the subject. In certain embodiments, the test subject has received therapeutic treatment for breast cancer (e.g., chemotherapy) prior to obtaining the second saliva sample, and in some cases, determining a comparative decrease in at least the first protein biomarker concentration in the second sample relative to the first sample indicates that the treatment regimen is effective.

The potential diagnostic benefits arising from embodiments of the invention include the overall management of breast cancer in women. The diagnosis of breast cancer at an earlier stage allows a woman more choice in selection of various treatment options. A saliva based test would be potentially useful in the postoperative management of cancer patients. In some embodiments of the above described methods, following tumor removal, a decrease in marker concentration will follow and eventually plateau to within a normal level indicating that the patient is free of disease. In contrast, a persistently high level of salivary markers will be indicative of tumor recurrence or persistence. In some embodiments, saliva is potentially a cost effective method for monitoring the effectiveness of chemotherapy, in which decreases in marker concentrations are observed if the treatment regimen is effective. These and other embodiments, features and potential advantages will become apparent with reference to the following description and drawings.

DEFINITIONS

In the following discussion and in the claims, the terms "comprising," "including" and "containing" are used in an open-ended fashion, and thus should be interpreted to mean "including, but not limited to . . . ".

The singular forms "a," "an," and "the" include plural referents unless the context clearly dictates otherwise.

The term "about," when used in the context of a numerical value, means approximately or reasonably close to the given number, and generally includes, but is not limited to, ±10% of the stated number.

The term "secondary to carcinoma of the breast," when referring to one or more up-regulated or down-regulated proteins, means resulting from metabolic or regulatory effects on the other tissues, fluids or structures due to carcinoma of the breast.

The term "salivary proteome" refers to the complement of proteins and peptides expressed in the saliva of a subject at a particular time and under given conditions.

The term "concentration value" refers to a quantitative amount or any other appropriate indication of a concentration, such as, for example, a colorimetric indicator score (e.g., +/−).

DETAILED DESCRIPTION

It was investigated in the present studies whether protein-by-products secondary to cancer related oncogenes that are over or under expressed appear in the saliva of breast cancer patients. It is proposed that saliva is a fluid suffused with solubilized protein by-products of oncogenic expression and these proteins are modulated secondary to ductal carcinoma in situ (DCIS) of the breast. Additionally, there are salivary protein profiles that are unique to both DCIS and fibroadenoma tumors. Such differences between DCIS and fibroadenoma are potentially valuable for noninvasively detecting and diagnosing breast cancer.

Saliva was selected for investigation as a diagnostic fluid primarily for two reasons: 1) collection of saliva is a non-invasive procedure that can be conducted in any environment requiring no special skills or equipment; and 2) the physiology of the oral cavity is such that the flow of secreted fluid is continually flushing and refreshing the fluid content of the mouth. Therefore, the composition of the fluid at any moment temporally reflects the metabolic activity of the secretory elements generating that fluid. There are also significant potential advantages over the study of plasma. In plasma the concentration of proteins can vary over nine orders of magnitude, which severely diminishes the likelihood of detecting those proteins at the lower end of the scale. The second consideration is that blood is composed of peptides, proteins and cells that have half lives ranging from seconds to weeks or even a month or more. As a consequence, the presence of a given substance might not accurately reflect the current state of the organism.

Protein profiling was performed on three pooled, stimulated whole saliva specimens. One specimen consisted of pooled saliva from 10 healthy subjects, another specimen was a pooled saliva specimen from 10 benign tumor patients (fibroadenomas), and the third specimen was from 10 subjects diagnosed with ductal carcinoma in situ (DCIS). Fibroadenoma was selected due to its high prevalence among benign breast tumors. DCIS was selected as this represents the lowest detectable tumor load according to the AJCC Cancer Staging Handbook, Part VII Breast (13). The cancer cohort, internally, was estrogen, progesterone and Her2/neu receptor status negative as determined by the pathology report. All subjects were matched for age and race and were non-tobacco users.

Saliva Collection and Sample Preparation.

Stimulated whole salivary gland secretion is based on the reflex response occurring during the mastication of a bolus of food. Usually, a standardized bolus (1 gram) of paraffin or a gum base (generously provided by the Wrigley Co., Peoria, Ill.) is given to the subject to chew at a regular rate. The individual, upon sufficient accumulation of saliva in the oral cavity, expectorates periodically into a preweighed disposable plastic cup. This procedure is continued for a period of five minutes. The volume and flow rate is then recorded along with a brief description of the specimen's physical appearance, similar to the procedure described by Berkhed and Heintze (14). The cup with the saliva specimen is reweighed and the flow rate determined gravimetrically. This salivary collection method may be modified for more consistent protein analyses as described by Streckfus et al. (15). A protease inhibitor from Sigma Co (St. Louis, Mich., USA) is added along with enough orthovanadate from a 100 mM stock solution to bring its concentration to 1 mM. The treated samples are centrifuged for 10 minutes at approximately 15,000×g in a conventional table top centrifuge. The supernatant is divided into 1 ml aliquots and frozen at −80° C.

LC-MS/MS Mass Spectroscopy with Isotopic Labeling.

Mass spectrometry, liquid chromatography, analytical software and bioinformatics techniques are used to analyze complex salivary peptide mixtures, wherein such techniques are capable of detecting differences in abundance of a given protein of over 8 orders of magnitude, as described by Wilmarth et al. (16). For example, isotopic labeling coupled with liquid chromatography tandem mass spectrometry (IL-LC-MS/MS) to characterize the salivary proteome is employed as described by Gu et al. (17). The preferred method is a mass spectroscopy based method that uses isotope coding of complex protein mixtures such as tissue extracts, blood, urine or saliva to identify differentially expressed proteins, according to the method of Shevchenko, et al. (18). In this way, changes in the level of expression of a protein are readily identified, thus permitting the analysis of putative regulatory pathways and providing information regarding the pathological disturbances in addition to potential biomarkers of disease. In embodiments, the analysis is performed on a tandem QqTOF QStar XL mass spectrometer (Applied Biosystems, Foster City, Calif., USA) equipped with an LC Packings (Sunnyvale, Calif., USA) HPLC for capillary chromatography. The HPLC is coupled to the mass spectrometer by a nanospray ESI head (Protana, Odense, Denmark) for maximal sensitivity, as described by Shevchenko, et al. (18). An advantage of tandem mass spectrometry combined with LC is enhanced sensitivity and the peptide separations afforded by chromatography. Thus, even in complex protein mixtures, MS/MS data can be used to sequence and identify peptides by sequence analysis with a high degree of confidence.

Isotopic labeling of protein mixtures has proven to be a useful technique for the analysis of relative expression levels of proteins in complex protein mixtures such as plasma, saliva urine or cell extracts. There are numerous methods that are based on isotopically labeled protein modifying reagents to label or tag proteins to determine relative or absolute concentrations in complex mixtures. The higher resolution offered by the tandem Qq-TOF mass spectrometer is ideally suited to isotopically labeled applications. The recently introduced iTRAQ reagents (Applied Biosystems) are amino reactive compounds that are used to label peptides in a total protein digest of a fluid (17, 19, 20). The tag remains intact through TOF-MS analysis; however, it is revealed during collision induced dissociation by MSMS analysis. Thus, in the MSMS spectrum for each peptide there is a fingerprint indicating the amount of that peptide from each of the different protein pools. Since virtually all of the peptides in a mixture are labeled by the reaction, numerous proteins in complex mixtures are identified and can be compared for their relative concentrations in each mixture. Thus even in complex mixtures there is a high degree of confidence in the identification.

Salivary Protein Analyses with iTRAQ.

The saliva samples are thawed and immediately centrifuged to remove insoluble materials. The supernatant is assayed for protein using the Bio-Rad protein assay (Hercules, Calif., USA) and an aliquot containing 100 μg of each specimen is precipitated with 6 volumes of −20° C. acetone. The precipitate is resuspended and treated according to the iTRAQ™ manufacturer's instructions. Protein digestion and reaction with iTRAQ labels are carried out according to the manufacturer's instructions (Applied Biosystems, Foster City, Calif.). Briefly, the acetone precipitable protein is centrifuged in a table top centrifuge at 15,000×g for 20 minutes. The acetone supernatant is removed and the pellet resuspended in 20 μl dissolution buffer. The soluble fraction is denatured and disulfides reduced by incubation in the presence of 0.1% SDS and 5 mM TCEP (tris-(2-carboxyethyl) phosphine)) at 60° C. for one hour. Cysteine residues are blocked by incubation at room temperature for 10 minutes with MMTS (methyl methane-thiosulfonate). Trypsin is added to the mixture to a protein:trypsin ratio of 10:1. The mixture is incubated overnight at 37° C. The protein digests are labeled by mixing with the appropriate iTRAQ reagent and incubating at room temperature for one hour. On completion of the labeling reaction, the four separate iTRAQ reaction mixtures are combined. Since there are a number of components that might interfere with the LCMSMS analysis, preferably the labeled peptides are partially purified by a combination of strong cation exchange followed by reverse phase chromatography on preparative columns, employing techniques that are known in the art. The combined peptide mixture is diluted 10 fold with loading buffer (10 mM $KH_2PO_4$ in 25% acetonitrile at pH 3.0) and applied by syringe to an ICAT Cartridge-Cation Exchange column (Applied Biosystems, Foster City, Calif.) column that has been equilibrated with the same buffer. The column is washed with 1 ml loading buffer to remove contaminants. To improve the resolution of peptides during LCMSMS analysis, the peptide mixture is partially purified by elution from the cation exchange column in 3 fractions. Stepwise elution from the column is achieved with sequential 0.5 ml aliquots of 10 mM $KH_2PO_4$ at pH 3.0 in 25% acetonitrile containing 116 mM, 233 mM and 350 mM KCl respectively. The fractions are evaporated by Speed Vac to about 30% of their volume to remove the acetonitrile and then slowly applied to an Opti-Lynx Trap C18 100 µl reverse phase column (Alltech, Deerfield, Ill.) with a syringe. The column is washed with 1 ml of 2% acetonitrile in 0.1% formic acid and eluted in one fraction with 0.3 ml of 30% acetonitrile in 0.1% formic acid. The fractions are dried by lyophilization and resuspended in 10 µl 0.1% formic acid in 20% acetonitrile. Each of the three fractions is analyzed by reverse phase LCMSMS.

Reverse Phase LC-MS/MS.

The desalted and concentrated peptide mixtures are quantified and identified by nanoLC-MS/MS on an API QSTAR XL mass spectrometer (ABS Sciex Instruments) operating in positive ion mode. The chromatographic system consists of an UltiMate nano-HPLC and FAMOS autosampler (Dionex LC Packings). Peptides are loaded on a 75 µm×10 cm, 3 µm fused silica C18 capillary column, followed by mobile phase elution: buffer (A) 0.1% formic acid in 2% acetonitrile/98% Milli-Q water and buffer (B): 0.1% formic acid in 98% acetonitrile/2% Milli-Q water. The peptides are eluted from 2% buffer B to 30% buffer B over 180 minutes at a flow rate 220 nL/min. The LC eluent is directed to a NanoES source for ESI/MS/MS analysis. Using information-dependent acquisition, peptides are selected for collision induced dissociation (CID) by alternating between an MS (1 sec) survey scan and MS/MS (3 sec) scans. The mass spectrometer automatically chooses the top two ions for fragmentation with a 60 s dynamic exclusion time. The IDA collision energy parameters were optimized based upon the charge state and mass value of the precursor ions. For each saliva sample set there are three separate LCMSMS analyses.

The accumulated MSMS spectra are analyzed by ProQuant and ProGroup software packages (Applied Biosystems) using the SwissProt fasta database for protein identification. The ProQuant analysis is carried out with a 75% confidence cutoff with a mass deviation of 0.15 Da for the precursor and 0.1 Da for the fragment ions. The ProGroup reports are generated with a 95% confidence level for protein identification.

Bioinformatics.

The Swiss-Prot database is employed for protein identification while the PathwayStudio® bioinformatics software package is used to determine regulatory pathways and distribution of proteins according to function. Venn diagrams may be constructed, using, for example, the Venn Diagram Plotter software program presently available from the U.S. National Center for Research Resource (43). Graphic comparisons with log conversions and error bars for protein expression are produced using the ProQuant® software, for example.

Figure 1:
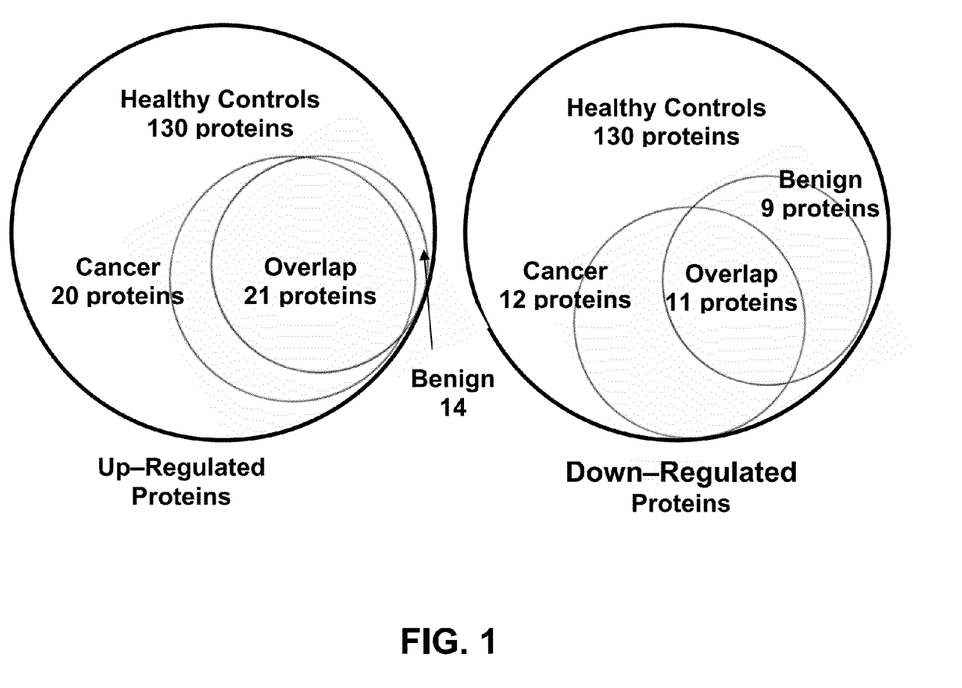
FIG. 1 is a set of Venn diagrams showing overlapping proteins between three groups of women, in accordance with an exemplary set of data illustrating an embodiment of the invention.

Table 1 summarizes the results of an exemplary iTRAQ analysis of saliva samples carried out as described above. Overall protein comparisons between benign vs. healthy, cancer vs. benign and cancer vs. healthy adult female subjects are shown. In total, 130 proteins were identified at a confidence level>95, and of those, 72 proteins were identified at >99 confidence level. Of these 130 proteins, there were 40 proteins that were determined to be expressed significantly differently ($p<0.05$) in the benign or tumor saliva compared to healthy controls. FIG. 1 is a Venn diagram of these proteins showing the overlapping proteins among the three groups of women.

Table 2 contains a list of the up-regulated (n=14) and down-regulated (n=9) proteins for the pooled saliva sample composed of individuals diagnosed with a fibroadenoma (benign tumor). The fold increase of protein and p-values are also presented. As shown in Table 2, of the 29 proteins, 9 (69%) were significant at the $p<0.001$ to $p<0.0001$ levels and 7 of those 9 proteins had a greater than 50% change in concentration.

Figure 2:
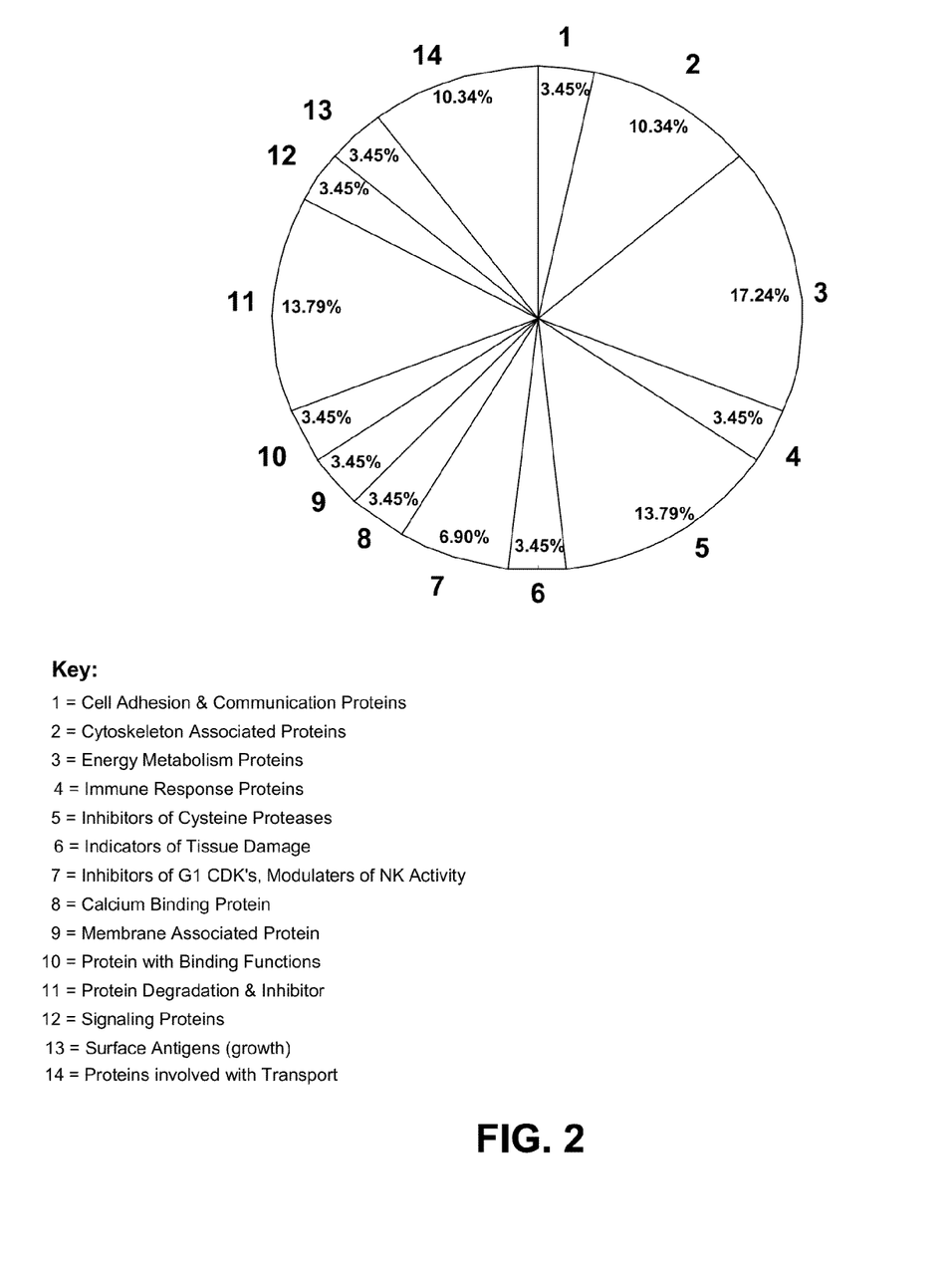
FIG. 2 is a chart showing the percentages of the 130 proteins from FIG. 1 that correspond to respective functions.

Table 3 contains a list of the up-regulated (n=20) and down-regulated (n=12) proteins observed in the Stage 0 cancer saliva compared to controls. "Stage 0 cancer" refers to breast tumor in which the stage is microscopic and demonstrates in situ involvement. The Stage 0 cancer saliva samples were obtained from women diagnosed with ductal carcinoma in situ. There were 15 proteins that showed a 1.5 fold increase in levels in the cancer compared to control subjects. Of these 15 differentially expressed proteins, 12 were significant at the $p<0.001$ to $p<0.0001$ levels. Each of the proteins listed in Table 3 is referenced in the literature as having been found in blood from cancer subjects and/or in cell supernatants from cancer cell lines. Of the 32 proteins that were up- or down-regulated secondary to carcinoma of the breast, 79% of those differentially expressed proteins are cited in the literature as being involved, molecularly, with breast cancer (27-36). The functions attributed to these proteins are shown in FIG. 2, along with an indication of the percentage of the total number of proteins that correspond to those respective functions.

Figure 3:
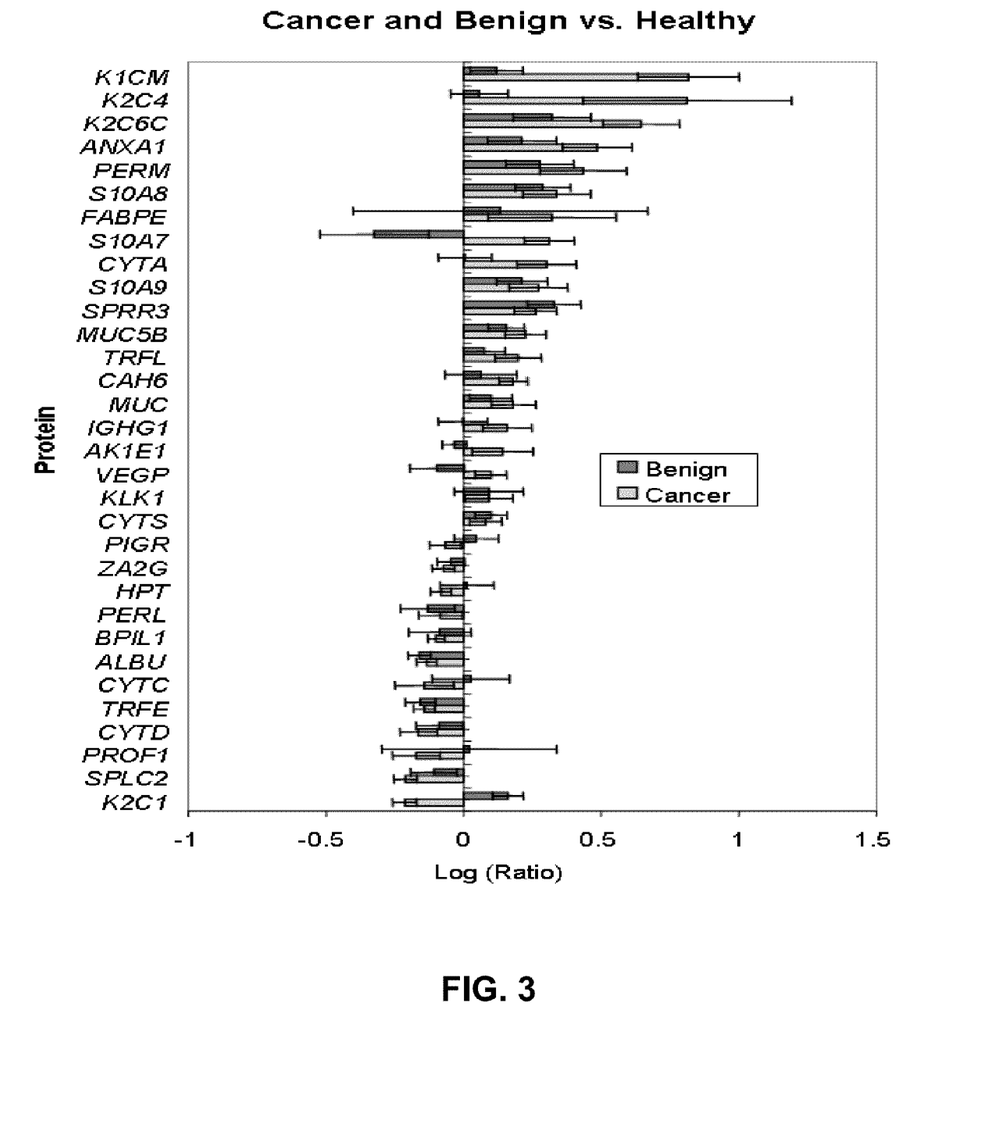
FIG. 3 is a chart showing the differential protein expression in cancer saliva (darker bars) or benign saliva (lighter bars) versus normal control represented by the 0 position.

A comparison of the differentially expressed proteins is shown in graphical form in FIG. 3. In this figure the log of the ratios for benign vs control and cancer vs control is plotted for each of the proteins. The error bars are the log of the error factor calculated by the ProQuant™ software. This comparison illustrates that there are a number of significant differences in the expression levels of several proteins between the cancer and benign saliva samples. A direct comparison of protein expression ratios between the benign and cancer pooled specimens that exhibited overlap or commonality among the proteins is shown in Table 4. Among the comparison of the overlapping proteins, the levels of 10 proteins fell at or below a p-value of 0.001 and the levels of 9 proteins represented a greater than 50% difference in the cancer saliva samples compared to benign saliva samples. These data are replotted in log form in FIG. 4.

In brief, three pooled (n=10 subjects/pool) stimulated whole saliva specimens from women were analyzed. One pooled specimen was from healthy women, another pooled specimen from women diagnosed with a benign breast tumor and the other one pooled specimen was from women diagnosed with ductal carcinoma in situ (DCIS). Differential expression of proteins was measured by isotopically tagging proteins in the tumor groups and comparing them to the healthy control group. Experimentally, saliva from each of the pooled samples was trypsinized and the peptide digests labeled with the appropriate iTRAQ reagent. Labeled peptides from each of the digests were combined and analyzed by reverse phase (C18) capillary chromatography on an Applied Biosystems QStar LC-MS/MS mass spectrometer equipped with an LC-Packings HPLC.

With respect to the overall analyses, the total number of salivary proteins reported in healthy individuals at the 95% confidence levels was 130 in the exemplary study disclosed herein. By comparison, in prior studies that used 2D gel and mass spectrometry, about 100-102 cancer-related salivary proteins were reported (16, 24). In still other prior studies, about 300 cancer-related salivary proteins were reported based on both 2D gel and "shotgun" proteomic techniques (21). Differences in the number of total proteins identified are probably a result of different technologies, profiling based on single samples or in collection and/or using single individual profiling (non-pooled specimen) or in collection and/or sampling techniques (37).

Of the 130 proteins presently identified in the saliva specimens, forty nine proteins were differentially expressed between the healthy control pool and the benign and cancer patient groups. Table 3 lists the proteins for the healthy pool vs. benign tumor pool, and Table 4 lists the proteins for the healthy pool vs. cancer tumor pool. As illustrated in Table 4, many of these proteins have been reported as being either up- or down-regulated in blood and cancer tissue. There is also an overlap of 13 up-regulated proteins and five down-regulated proteins between the protein profiles, leaving the benign group with five proteins that are unique to fibroadenomas (ENOA, IGHA2, IL-1 ra, S10A7, SPLC2) and 11 proteins unique to DCIS (CAH6, K2C4, CYTA, FABP4, IGHI, TRFL, BPIL1, CYTC, HPT, PROF1, ZA2G). FIG. 1 shows Venn diagrams of the overlapping proteins between the three groups of women. Notably, two-thirds of the total "overlap" proteins were up-regulated. Without wishing to be limited to any specific theory to explain this phenomenon, it is proposed that a portion of the up-regulated proteins that exhibited overlap are associated with pathways which are common to both disorders. This would include the proteins associated with cytoskeleton and cell growth. The benign tumor was targeted in order to increase the specificity of the panel of markers. If there are markers specific to a benign tumor and other markers specific only to the malignancy, then the probability of making the correct clinical assessment is further increased.

Tables 5, 6 and 7 represent a comparison of the healthy control and cancer proteins which overlapped each group. As illustrated in Tables 5-7, changes are listed in order of confidence, level 3 being the highest confidence. Confidence levels are defined as follows: Level 3: Changes greater than 2 fold from good quality signals that also pass a visual inspection. Level 2: Changes greater than 2 fold from good quality signals that do not pass visual inspection. Level 1: Changes greater than 2 fold from low quality signals. Level 0: No significant protein changes.

Figure 4:
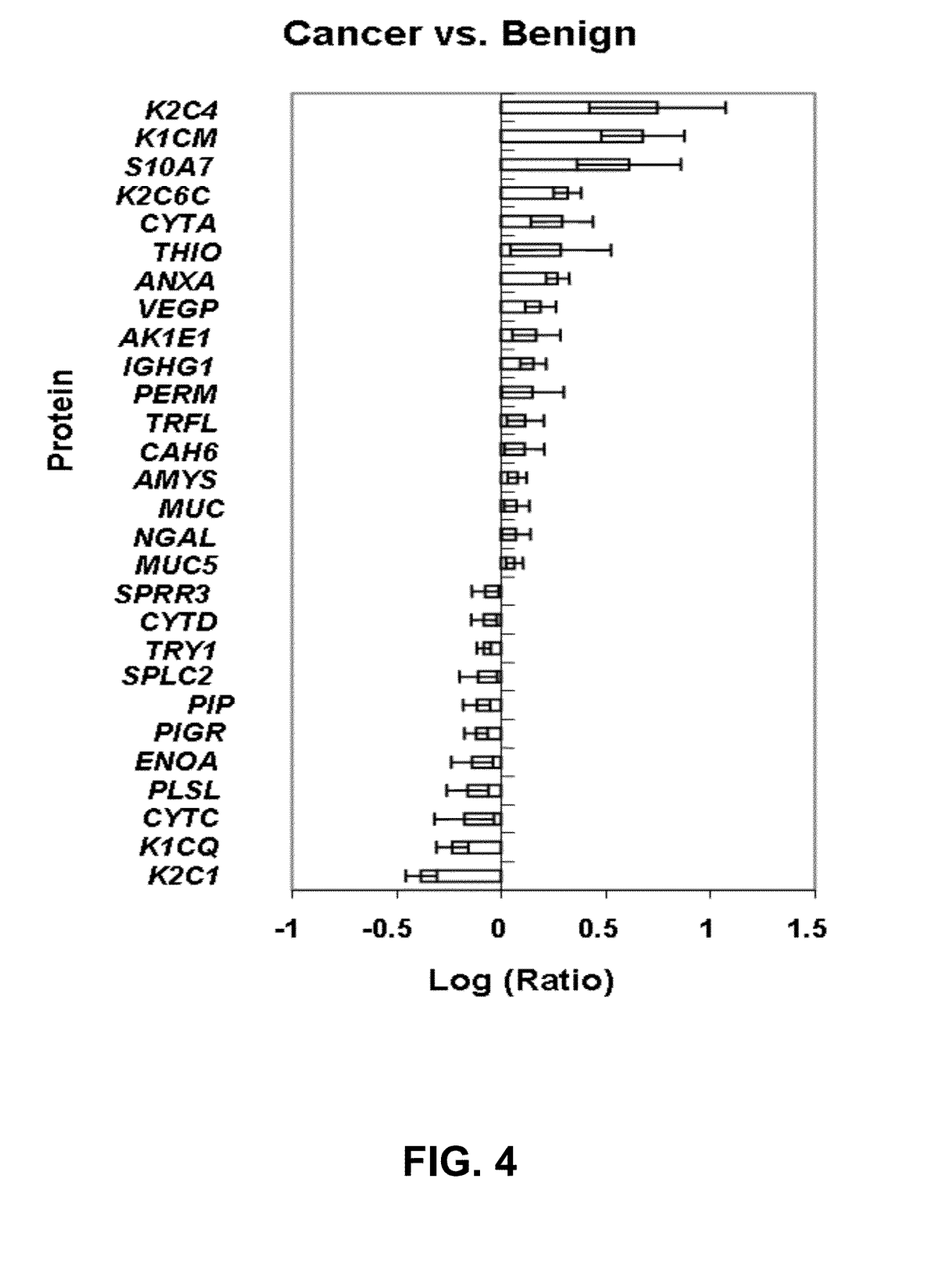
FIG. 4 is a chart showing the differential protein expression in cancer saliva (bars) versus benign saliva represented by the 0 position.

In this comparison, only seven proteins remained significantly different in the presence of carcinoma ($p \le 0.005$). This would include the proteins associated with exocytosis, the cytoskeleton and immuno-response. As the cell proliferation process is further enhanced in the presence of carcinoma, these proteins are expected to be significantly up-regulated in the case of carcinoma. FIGS. 3 and 4 provide further illustration of the protein comparisons.

Without wishing to be limited to a single theory to explain the mechanism by which these proteins are altered in the presence of carcinoma of the breast, it is proposed that since the histo-physiology is very similar between the ductal tissues of the breast and those of the salivary glands, there may be extra-cellular communication between the two distant tissues (38, 39). This phenomenon has also been observed in nipple aspirates (40, 41) which have yielded many of the same protein constituents as observed in Table 4.

The salivary proteome that is altered in the presence of carcinoma of the breast was examined in the present studies, and a group of proteins were identified that have potential diagnostic utility for breast cancer. Saliva as a diagnostic media has potential clinical advantages because it contains numerous proteins and protein fragments that may have analytical value. Salivary fluid is continually produced and excreted in an open-ended circuit, thereby offering a way to obtain "real-time" results. In contrast, blood exists in a "closed-loop" system. Therefore blood, as a circulating media, may contain proteins that are a day, a week, or a month old as well as proteins which have passed numerous times through many organ systems or have been excreted (42). In some cases, saliva and nipple aspirates may be a more useful diagnostic fluid than blood.

Use of Salivary Biomarkers to Differentiate Non-Cancerous Tissue, Benign Tumor, and DCIS in a Test Sample.

In some embodiments, one or more salivary biomarkers are used to differentiate non-cancerous breast tissue, benign breast tumor and ductal carcinoma in situ of the breast by analyzing the salivary proteome of an individual suspected of having breast cancer, as described above. One or more of the protein biomarkers identified in Tables 3 and 4 are identified and quantified in the test patient's saliva specimen, and the resulting values are then compared to a biomarker reference panel, which is developed in accordance with the above-described procedure. The biomarker reference panel is made up of a group of the same saliva protein constituents developed using DCIS, benign tumor and healthy, non-cancerous (i.e., tumor free) control group populations. Each constituent has associated with it a range of concentration values, a mean concentration, and statistical error range. Receiver Operating Characteristic Curves (ROC) curves (sensitivity vs. 1-specificity) are constructed for salivary protein concentrations. The optimum cutoff value for each marker is determined by using the cutoff value that produces the largest percentage of area under its ROC curve. The salivary ROC curves for each marker are compared using a modified Wilcoxon rank sum procedure. Once determinations have been made for the sensitivity and specificity of each marker, positive and negative predictive values, and likelihood ratios are calculated. The same types of analyses are also made for the benign tumor group versus the cancer group. From comparison of the individual marker values to the reference panel values, a differential diagnosis of the patient is determined.

For individual protein biomarker values that fall within the range of control values, a diagnosis of lower risk or likelihood of occurrence of breast tumor is determined. A comparison chart similar to that shown in FIG. 3 or 4 may be employed, for example, in which the reference values of the biomarkers in breast tumor saliva samples are presented relative to controls (e.g., mean values for saliva samples from breast tumor-free individuals). Alternatively, the reference values may be stored electronically on a computer readable storage device, and a computer aided comparison is performed and a diagnostic report is prepared, upon input of the test sample biomarker levels. When the concentration value of a selected protein biomarker falls within the range for that protein in the DCIS and/or benign groups of the reference panel, a diagnosis of elevated risk or likelihood of the presence or occurrence of a breast tumor is appropriate. When the concentration of a protein is significantly different than the mean concentration of the same protein in the control group of the reference panel, a diagnosis of high risk or high likelihood of the presence of a breast tumor, or of the occurrence of a breast tumor, is appropriate.

In one embodiment of a screening procedure, the biomarker Q9UBC9/SPRR3 (encoded by GenBank Accession No. Q9UBC9 Gene ID. SPRR3), indicated in Tables 3 and 4, is quantitated in the saliva of an individual to diagnose a breast cancer, using the above-described saliva sample preparation and analysis procedures, or equivalent methods. The detected level or value of the biomarker is then compared to reference values of the biomarker in the saliva of individuals with breast tumors (either benign fibroadenomas or DCIS). By comparison of the individual's marker value to the reference value (or range of values), a differential diagnosis of the patient is determined, to differentiate between breast cancer and breast cancer-free condition.

In a modification of this procedure, the individual's salivary level of the Q9UBC9/SPRR3 biomarker is additionally compared to respective reference values in the saliva of individuals with DCIS and of individuals with benign breast tumor (i.e., fibroadenoma). By further comparison of the individual's marker value to the respective reference values of the marker in individuals with DCIS or benign breast tumor, a further diagnosis of the patient is obtained, to differentiate between benign breast tumor and DCIS.

In another embodiment the biomarker Q8N4F0/BPIL1 (encoded by GenBank Accession No. Q8N4F0 Gene ID. BPIL1), indicated in Table 3, is quantitated in the saliva of an individual to diagnose DCIS breast tumor, using the above-described saliva sample preparation and analysis procedures, or equivalent methods. The detected level of the biomarker is then compared to respective reference values of the biomarker in the saliva of individuals with DCIS and of individuals with benign breast tumor (i.e., fibroadenoma). By comparison of the individual's marker value to the reference values, a differential diagnosis of the patient is determined, to differentiate between tumor-free breast tissue and a breast cancer, or to indicate lower risk or likelihood of the presence or occurrence, if the value of the test sample falls within the control values for this protein biomarker.

In another embodiment the biomarker P07737/PROF1 (encoded by GenBank Accession No. P07737 Gene ID. PROF1), indicated in Table 3, is quantitated in the saliva of an individual to diagnose benign or DCIS breast tumor, using the above-described saliva sample preparation and analysis procedures, or equivalent methods. The detected level of the biomarker is then compared to respective reference values of the biomarker in the saliva of individuals with DCIS and of individuals with benign breast tumor (i.e., fibroadenoma). By comparison of the individual's marker value to the reference values, a differential diagnosis of the patient is determined, to differentiate between tumor-free breast tissue and a breast tumor (either benign or DCIS). As noted above, if the value of the test sample falls within the control values for this protein biomarker, a diagnosis of lower risk or likelihood of the presence or occurrence of either fibroadenoma or DCIS is made.

Another embodiment uses the biomarker P01024/C03 (encoded by GenBank Accession No. P01024 Gene ID. 003). No. P01024 Gene ID C03 is important due to its central role in the activation of the classical complement system and contributes to innate immunity. Its activation is required and generally results in an early inflammatory response. As DCIS is a very early stage carcinoma and localized inflammation may be initially present, this protein will present itself as a marker for early detection. This biomarker is quantitated in the saliva of an individual using the above-described saliva sample preparation and analysis procedures, or equivalent methods. The detected level of the biomarker is then compared to reference value of the biomarker in the saliva of individuals with DCIS. By comparison of the individual's marker value to the reference value, a diagnosis of the patient is determined, to differentiate between tumor-free breast tissue and DCIS. As noted above, if the value of the test sample falls within the control values for this protein biomarker, a diagnosis of lower risk or likelihood of the presence or occurrence of DCIS is made. This biomarker is not typically associated with benign tumors. Therefore, in some screening applications, the comparative values of the P01024/C03 biomarker in an individual's saliva will be especially informative as to the likelihood of the risk or present existence of DCIS in that individual.

In variations of the foregoing embodiments, quantitation and analysis of two or more of the above-identified biomarkers are combined to increase the robustness of the diagnostic test. For example, a screening procedure may analyze the comparative levels of Q9UBC9/SPRR3 and one or more biomarkers that are essentially unique to fibroadenomas (e.g., ENOA, IGHA2, IL-1ra, S10A7, SPLC2). In some cases, a screening procedure may analyze the comparative levels of Q8N4F0/BPIL1 and one or more biomarkers that are essentially unique to DCIS (e.g., CAH6, K2C4, CYTA, FABP4, IGHGI, TRFL, BPIL1, CYTC, HPT, PROF1 and ZA2G), in an individual's saliva sample. In some cases, a screening procedure may analyze the comparative levels of P07737/PROF1 or P01024/C03 in an individual's saliva relative to the respective biomarker value in control saliva samples, to determine a diagnosis of the patient that differentiates between tumor-free breast tissue and breast tumor.

It is believed that the protein biomarkers Q9UBC9/SPRR3, Q8N4F0/BPIL1, P07737/PROF1 and P01024/C03 have not been previously associated with breast tumors. They are believed to primarily function, respectively, as an indicator of tissue damage, as a transport protein, i.e. associated with movement of proteins across a cellular membrane, as a cytoskeleton-associated protein, and as an initiator of immune responses. The combined screening for saliva levels of variously-functioning protein biomarkers such as these potentially offers a more robust diagnostic method than a method that screens for protein biomarkers associated with only a single physiological function. Additionally, using multiple biomarkers enhances cancer detection by reducing the number of false positives and negatives. This is achieved by using proteins that are associated uniquely with specific biological pathways, markers that are tumor specific (benign vs. malignant), and by determining if the proteins are up- or down-regulated in the presence of disease. Collectively, this information will reduce subjectivity and provide the clinician with information for superior clinical decision-making.

Accordingly, in another embodiment of a diagnostic screening procedure, one or more of the biomarkers Q9UBC9/SPRR3, Q8N4F0/BPIL1, P07737/PROF1 and P01024/C03 are quantitated and analyzed along with another biomarker, such as a biomarker that is known to be significantly up-regulated or down-regulated in benign breast tumors and/or DCIS (e.g., significant at the $p<0.001$ to $p<0.0001$ level). Such other biomarkers include, for example, those that are known to be associated with cell adhesion and/or communication; are associated with the cytoskeleton; are involved with energy metabolism; are associated with immune response; are inhibitors of cysteine proteases; are indicators of tissue damage; inhibit G1 CDKs, or modulate NK activity; are calcium binding proteins; are membrane associated proteins; are proteins with binding functions; are involved with protein degradation and inhibition; are associated with cell signaling; are surface antigens related to growth; or are involved with transport in cells of the body. Some specific examples of such biomarkers are identified in Tables 3 and 4.

A patient may be monitored for recurrence or progression of breast cancer after surgery, by testing the status of saliva biomarkers before and after surgery, and periodically thereafter. Such differential identifications may be used alone or in conjunction with one or more other diagnostic methods for diagnosing or monitoring a patient for breast cancer. For instance, the patient may have received therapeutic treatment for breast cancer, with or without prior surgical removal of cancerous tissue. Analyzing saliva samples for protein biomarkers, in accordance with the methods described herein, will potentially aid in making treatment decisions for the patient. The effectiveness of a given drug, or radiation therapy, or surgical procedure may be monitored by periodically determining the status of the saliva biomarkers in the patient, and comparing them to the same reference panel and/or to the patient's previous saliva tests.

The potential diagnostic benefits include the overall management of breast cancer in women. The diagnosis of breast cancer at an earlier stage allows a woman more choice in selection of various treatment options. A saliva based test is potentially useful in the postoperative management of cancer patients. For example, in some cases, following tumor removal, a decrease in marker concentration will follow and eventually plateau to within a normal level indicating that the patient is free of disease. In contrast, a persistently high level of salivary protein biomarkers will be indicative of tumor recurrence or persistence. Saliva is potentially a cost effective method for monitoring the effectiveness of chemotherapy in which decreases in marker concentrations are observed if the treatment regimen is effective.

TABLE 1

| Comparison | Up Regulated | Down Regulated | Total Markers |
|---|---|---|---|
| Benign vs. Healthy | 14 | 9 | 23 |
| Cancer vs. Healthy | 20 | 12 | 32 |
| Cancer vs. Benign | 17 | 11 | 28 |
| Totals | 51 | 32 | 83 |

TABLE 2

Benign vs. Healthy

| Accession | Protein Name | Ratio | p Value | Gene ID. |
|---|---|---|---|---|
| Up-Regulated Proteins in Benign | | | | |
| P06733 | Alpha enolase | 1.4204 | 0.0006 | ENOA |
| P04083 | Annexin A1 | 1.6282 | 0.0047 | ANXA1 |
| P05109 | Calgranulin A | 1.9393 | 0.0001 | S10A8 |
| P06702 | Calgranulin B | 1.6297 | 0.0002 | S10A9 |
| Q9UBC9 | Cornifin beta | 2.1353 | 0.0000 | SPRR3 |
| P01036 | Cystatin S precursor | 1.2584 | 0.0027 | CYTS |
| P01877 | Ig alpha-2 chain C region | 1.2781 | 0.0213 | IGHA2 |
| P01871 | Ig mu chain C region | 1.256 | 0.0196 | MUC |
| P13646 | Keratin, type I cytoskeletal 13 | 1.3184 | 0.0180 | K1CM |
| Q9QWL7 | Keratin, type I cytoskeletal 17 | 2.6008 | 0.0018 | K1CQ |
| P04264 | Keratin, type II cytoskeletal 1 | 1.4504 | 0.0002 | K2C1 |
| P48666 | Keratin, type II cytoskeletal 6C | 2.0979 | 0.0003 | K2C6C |
| Q9HC84 | Mucin 5B precursor | 1.4306 | 0.0001 | MUCSB |
| P05164 | Myeloperoxidase precursor | 1.8949 | 0.0015 | PERM |
| Down-Regulated Proteins in Benign | | | | |
| P28325 | Cystatin D precursor | 0.817 | 0.0455 | CYTD |
| P18510 | Interleukin-1 receptor antagonist protein precursor | 0.7484 | 0.0312 | IL1RA |
| P22079 | Lactoperoxidase precursor | 0.7408 | 0.0137 | PERL |
| P80188 | Neutrophil gelatinase-associated lipocalin precursor | 0.7971 | 0.0289 | NGAL |
| P31151 | S100 calcium-binding protein A7 | 0.4737 | 0.0054 | S10A7 |
| P04745 | Salivary alpha-amylase precursor | 0.8245 | 0.0023 | AMYS |
| P02787 | Serotransferrin precursor | 0.6968 | 0.0000 | TRFE |
| P02768 | Serum albumin precursor | 0.6922 | 0.0000 | ALBU |
| Q96DR5 | Short palate, lung and nasal epith. Ca assoc.protein 2 | 0.7798 | 0.0170 | SPLC2 |

TABLE 3

Cancer vs. Healthy

| Accession Number | Protein Name | Ratio | P Value | Gene ID | Reported Function | Blood (Ref.) | Tissue (Ref.) |
|---|---|---|---|---|---|---|---|
| Up-Regulated Proteins in Cancer Saliva | | | | | | | |
| Q9DCT1 | Aldo-keto reductase | 1.44 | 0.0264 | AK1E1 | Detox & reduction | — | 25 |
| P04083 | Annexin A1 | 3.06 | 0.0001 | ANXA1 | Membrane associated protein | 30 | 25 |
| P05109 | Calgranulin A | 2.18 | 0.0001 | S10A8 | Cell adhesion & communication | 30 | — |
| P06702 | Calgranulin B | 1.87 | 0.0001 | S10A9 | Cell adhesion & communication | 30 | — |
| P23280 | Carbonic anhydrase VI | 1.52 | 0.0003 | CAH6 | Energy/metabolism | 30 | 27 |
| Q9UBC9 | Cornifin beta | 1.82 | 0.0001 | SPRR3 | Indicator of tissue damage | — | — |
| P13646 | Cytokeratin 13 | 6.56 | 0.0001 | K1CM | Intracytoplasmatic cytoskeleton protein | 30 | — |
| P19013 | Cytokeratin 4 | 6.50 | 0.0019 | K2C4 | Intracytoplasmatic cytoskeleton protein | 30 | 25 |

TABLE 3-continued

Cancer vs. Healthy

| Accession Number | Protein Name | Ratio | P Value | Gene ID | Reported Function | Blood (Ref.) | Tissue (Ref.) |
|---|---|---|---|---|---|---|---|
| P48666 | Cytokeratin 6C | 4.41 | 0.0001 | K2C6C | Intracytoplasmatic cytoskeleton protein | — | — |
| P01040 | Cystatin A | 2.00 | 0.0014 | CYTA | Protein degradation & inhibitor | 30 | 25 |
| P01036 | Cystatin SA-III | 1.20 | 0.0115 | CYTS | Protein degradation & inhibitor | — | — |
| Q01469 | Epid. Fatty acid-binding prot. | 2.1 | 0.0362 | FABP4 | Protein with binding functions | 30 | — |
| P01857 | Ig gamma-1 chain C region | 1.44 | 0.0034 | IGHG1 | Immunoresponse | — | — |
| P01871 | Ig mu chain C region | 1.51 | 0.0011 | MUC | Immunoresponse | — | — |
| P06870 | Kallikrein 1 precursor | 1.23 | 0.0425 | KLK1 | Serine protease | — | — |
| P02788 | Lactoferrin | 1.58 | 0.0001 | TRFL | Inhibits G1 CDK's, mod. NK activity | 30 | 26 |
| Q9HC84 | Mucin 5B | 1.68 | 0.0001 | MUC5B | Cell adhesion & communication | — | 36 |
| P05164 | Myeloperoxidase precursor | 2.72 | 0.0005 | PERM | Defense Immunoresponse | 30 | — |
| P31151 | S100 calcium-binding protein | 2.05 | 0.0001 | S100P | Calcium binding protein | 30 | 25 |
| P31025 | Von Ebner's gland protein (lipocalin) | 1.26 | 0.0043 | VEGP | Inflammation | — | 25 |
| Down-Regulated Proteins in Cancer Saliva ||||||||
| Q8N4F0 | Bact. Perm.-increasing prot.-1 | 0.80 | 0.0004 | BPIL1 | Transport | 30 | — |
| P04264 | Cytokeratin 1 | 0.61 | 0.0001 | K2C1 | Intracytoplasmatic cytoskeleton protein | — | 25 |
| P01034 | Cystatin C | 0.72 | 0.0187 | CYTC | Inhibitor of cysteine proteases | — | 31 |
| P28325 | Cystatin D precursor | 0.68 | 0.001 | CYTD | Protein degradation & inhibitor | — | — |
| P00738 | Haptoglobin | 0.83 | 0.0023 | HPT | Indicator of tissue damage and necrosis | 30, 34 | — |
| P22079 | Lactoperoxidase | 0.82 | 0.0388 | PERL | Transport | — | 33 |
| P01833 | Poly-IG receptor protein | 0.86 | 0.0234 | PIGR | Immunoresponse | — | — |
| P07737 | Profilin-1 | 0.68 | 0.0135 | PROF1 | Cytoskeleton associated | — | 25 |
| P02768 | Serum albumin precursor | 0.73 | 0.0001 | ALBU | Transport | 30 | 27 |
| Q96DR5 | Short palate, lung and nasal epith. carc. assoc. protein 2 | 0.61 | 0.0001 | SPLC2 | Immune response & detox. | — | 32 |
| P02787 | Transferrin | 0.72 | 0.0001 | TRFE | Surface antigen assoc. with growth | 34 | — |
| P25311 | Zinc-alpha-2-glycoprotein | 0.84 | 0.0009 | ZA2G | Signaling | — | 29 |

TABLE 4

Cancer vs. Benign

| Accession | Protein Name | Ratio | p Value | Gene ID. |
|---|---|---|---|---|
| Up-Regulated Proteins in Cancer |||||
| Q9HC84 | Mucin 5B precursor | 1.16 | 0.0046 | MUC5B |
| P80188 | lipocalin precursor | 1.18 | 0.0443 | NGAL |
| P01871 | Ig mu chain C region | 1.19 | 0.0231 | MUC |
| P04745 | Salivary alpha-amylase precursor | 1.19 | 0.001 | AMYS |
| P23280 | Carbonic anhydrase VI precursor | 1.29 | 0.0293 | CAH6 |
| P02788 | Lactotransferrin precursor | 1.30 | 0.0113 | TRFL |
| P05164 | Myeloperoxidase precursor | 1.41 | 0.0487 | PERM |
| P01857 | Ig gamma-1 chain C region | 1.43 | 0.0004 | IGHG1 |
| Q9DCT1 | Aldo-keto reductase | 1.47 | 0.018 | AK1E1 |
| P31025 | Von Ebner's gland protein | 1.55 | 0.0005 | VEGP |
| P04083 | Annexin A1 | 1.86 | 0 | ANXA1 |
| P10599 | Thioredoxin | 1.93 | 0.03 | THIO |
| P01040 | Cystatin A | 1.95 | 0.0056 | CYTA |
| P48666 | Keratin, type II cytoskeletal 6C | 2.07 | 0 | K2C6C |
| P31151 | S100 calcium-binding protein A7 | 4.08 | 0.0005 | S10A7 |
| P13646 | Keratin, type I cytoskeletal 13 | 4.76 | 0 | K1CM |
| P19013 | Keratin, type II cytoskeletal 4 | 5.59 | 0.0013 | K2C4 |
| Down-Regulated Proteins in Cancer |||||
| P04264 | Keratin, type II cytoskeletal 1 | 0.42 | 0 | K2C1 |
| Q9QWL7 | Keratin, type I cytoskeletal 17 | 0.58 | 0.001 | K1CQ |
| P01034 | Cystatin C precursor | 0.67 | 0.0246 | CYTC |
| P13796 | L-plastin | 0.69 | 0.0145 | PLSL |
| P06733 | Alpha enolase | 0.73 | 0.0106 | ENOA |
| P01833 | Polymeric-Ig receptor | 0.76 | 0.0002 | PIGR |
| P12273 | Prolactin-inducible protein precursor | 0.77 | 0.0012 | PIP |
| Q96DR5 | Short palate, lung and nasal epithelium carcinoma associated protein 2 precursor | 0.78 | 0.0219 | SPLC2 |
| P07477 | Trypsin I precursor | 0.82 | 0.0196 | TRY1 |
| P28325 | Cystatin D precursor | 0.83 | 0.0155 | CYTD |
| Q9UBC9 | Small proline-rich protein 3 | 0.84 | 0.0228 | SPRR3 |

TABLE 5

Low risk Subjects vs. Stage 0 Cancer Subjects
Level 3 - Changes greater than 2-fold from good quality signals that pass a visual inspection

| SSP | Acc. No. | Type | Lane | Protein Name | Level | Swiss Prot ID | Locus | Predicted MW | MW | Signal | Change | FoldChange |
|---|---|---|---|---|---|---|---|---|---|---|---|---|
| 5602 | A13920 | CONTROL | 25 | Annexin I | 3 | P46193 | 301 | 38 | 40 | 0 | − | 26.65 |
| 2501 | A14020 | CONTROL | 5 | Annexin II | 3 | P07355 | 302 | 36 | 39 | 1 | − | div/0 |
| 6903 | A92820 | CONTROL | 27 | Apaf-1 | 3 | O14727 | 317 | 130 | 137 | 1 | − | div/0 |
| 5702 | R10820 | CONTROL | 22 | BAG-1-58KD | 3 | Q99933 | 573 | 50/46/33 | 58 | 1 | − | 12.90 |
| 6601 | C41720 | CONTROL | 27 | Calreticulin-51KD | 3 | P14211 | 12317 | 60 | 51 | 1 | − | div/0 |
| 6702 | C41720 | CONTROL | 27 | Calreticulin-54KD | 3 | P14211 | 12317 | 60 | 54 | 1 | − | div/0 |
| 9703 | C20820 | CANCER | 30 | E-Cadherin | 3 | P12830 | 999 | 120 | 120 | 1 | − | div/0 |
| 5901 | N38620 | CONTROL | 23 | eNOS/NOS Type III | 3 | P29474 | 4846 | 140 | 140 | 1 | − | div/0 |

TABLE 5-continued

Low risk Subjects vs. Stage 0 Cancer Subjects
Level 3 - Changes greater than 2-fold from good quality signals that pass a visual inspection

| SSP | Acc. No. | Type | Lane | Protein Name | Level | Swiss Prot ID | Locus | Predicted MW | MW | Signal | Change | FoldChange |
|---|---|---|---|---|---|---|---|---|---|---|---|---|
| 3901 | C26220 | CONTROL | 9 | g-Catenin | 3 | Q15151 | 3728 | 82 | 82 | 1 | − | div/0 |
| 6401 | G16720 | CONTROL | 28 | GRB2 | 3 | P29354 | 81504 | 24 | 24 | 0 | + | 3.09 |
| 8401 | G16720 | CONTROL | 33 | GRB2-24KD | 3 | P29354 | 81504 | 24 | 24 | 1 | + | 3.86 |
| 8501 | G16720 | CONTROL | 33 | GRB2-28KD | 3 | P29354 | 81504 | 24 | 28 | 0 | + | 10.15 |
| 1601 | M93620 | CANCER | 5 | Mint3/X11g-61KD | 3 | O88888 | 9546 | 61 | 61 | 0 | + | 4.65 |
| 4904 | M94120 | CONTROL | 14 | MSH3-138KD | 3 | P20585 | 4437 | 127 | 138 | 1 | − | div/0 |
| 3607 | P35220 | CONTROL | 7 | PP1 | 3 | P08129 | 5499 | 36 | 41 | 1 | − | 2.18 |
| 202 | R23520 | CANCER | 2 | Ral A | 3 | P11233 | 5898 | 24 | 26 | 1 | − | 21.01 |
| 2101 | S10520 | CANCER | 8 | Spot 14 | 3 | Q92746 | 7069 | 17 | 17 | 0 | + | 2.00 |
| 2601 | T57120 | CONTROL | 2 | Tau-53KD | 3 | P10636 | 4137 | 50-68 | 53 | 1 | + | 3.02 |

TABLE 6

Low risk Subjects vs. Stage 0 Cancer Subjects
Level 2 - Changes greater than 2-fold from good quality signals that do not pass a visual inspection

| SSP | Acc. No. | Type | Lane | Protein Name | Level | Swiss Prot ID | Locus | Predicted MW | MW | Signal | Change | FoldChange |
|---|---|---|---|---|---|---|---|---|---|---|---|---|
| 7503 |  | CANCER | 20 | alpha-Tubulin | 2 | 0 | 0 | 55 | 58 | 1 | − | 1.92 |
| 5504 | F14220 | CONTROL | 23 | basic FGF-25KD | 2 | P09038 | 2246 | 18-24 | 25 | 1 | + | 3.30 |
| 6602 | C80420 | CONTROL | 29 | CD38 | 2 | P28907 | 952 | 46 | 41 | 1 | − | div/0 |
| 4601 | C45820 | CONTROL | 17 | CDC25B-53KD | 2 | O43550 | 994 | 63 | 53 | 0 | + | 2.20 |
| 7702 | F19720 | CONTROL | 30 | fyn | 2 | P06241 | 2534 | 59 | 55 | 0 | + | 3.51 |
| 4501 | G59720 | CONTROL | 14 | GST-p | 2 | P09211 | 2950 | 23 | 25 | 1 | + | 3.89 |
| 7404 | H10520 | CANCER | 20 | KNP-1/HES1 | 2 | 0 | 0 | 28 | 28 | 1 | − | 4.38 |
| 7601 | L15620 | CONTROL | 31 | lck-53KD | 2 | P06239 | 3932 | 56 | 53 | 1 | + | 3.67 |
| 2301 | N13320 | CANCER | 8 | NES1 | 2 | O43240 | 5655 | 30 | 28 | 0 | − | 2.00 |
| 4201 | N42420 | CONTROL | 20 | NTF2 | 2 | 0 | 0 | 15 | 15 | 0 | + | 1.89 |
| 3402 | P11920 | CONTROL | 9 | p24 | 2 | P97799 | 22360 | 24 | 24 | 1 | + | 4.48 |
| 5608 | A36520 | CONTROL | 26 | Phospho-Akt (S473) | 2 | P31749 | 207 | 59 | 54 | 0 | + | 3.89 |
| 3610 | P67920 | CONTROL | 7 | PKBa/Akt-53KD | 2 | P31749 | 207 | 59 | 53 | 1 | + | 2.56 |
| 7608 | P97220 | CANCER | 21 | PKR | 2 | Q03963 | 54287 | 58 | 62 | 1 | + | 31.10 |
| 9201 |  | CANCER | 35 | Rap2 | 2 | 0 | 0 | 21 | 21 | 1 | − | div/0 |
| 6501 | R73920 | CONTROL | 29 | Rho-25KD | 2 | P03749 | 387 | 21 | 25 | 1 | + | 3.06 |
| 6607 | R41220 | CANCER | 14 | RIP | 2 | Q13546 | 8737 | 74 | 66 | 1 | − | 2.16 |

TABLE 7

Low risk Subjects vs. Stage 0 Cancer Subjects
Level 1 - Changes greater than 2-fold from low quality signals

| SSP | Acc. No. | Type | Lane | Protein Name | Level | Swiss Prot ID | Locus | Predicted MW | MW | Signal | Change | FoldChange |
|---|---|---|---|---|---|---|---|---|---|---|---|---|
| 7406 | 556596 | CANCER | 24 | 14-3-3 | 1 | Q9S928 | 55948 | 30 | 30 | 2 | + | 3.22 |
| 2603 | A27320 | CANCER | 11 | Acetylcholinesterase | 1 | P22303 | 43 | 68 | 60 | 2 | + | 104.25 |
| 8503 | A40720 | CONTROL | 33 | ApoE | 1 | P02649 | 348 | 36 | 36 | 2 | − | div/0 |
| 9503 | A37720 | CANCER | 35 | Arp3 | 1 | 0 | 0 | 50 | 51 | 2 | − | 5.64 |
| 9601 | A37720 | CONTROL | 37 | Arp3 | 1 | 0 | 0 | 50 | 50 | 2 | − | 2.70 |
| 901 | G73320 | CONTROL | 1 | BiP/GRP78 | 1 | P11021 | 3309 | 78 | 74 | 2 | + | 2.24 |
| 9508 | C41720 | CANCER | 35 | Calreticulin | 1 | 0 | 0 | 60 | 60 | 2 | + | 2.26 |
| 7504 | C14520 | CANCER | 22 | Csk | 1 | P32577 | 64019 | 50 | 56 | 2 | − | 50.52 |
| 1701 | C37020 | CANCER | 4 | E-Cadherin | 1 | P12830 | 999 | 120 | 120 | 2 | − | div/0 |
| 2602 | H62120 | CANCER | 10 | MLP/XIAP | 1 | P98170 | 331 | 57 | 60 | 2 | + | 1.99 |
| 1404 | H22020 | CANCER | 5 | Hsp40 | 1 | P25685 | 3301 | 40 | 43 | 2 | + | 2.09 |
| 1501 | M93620 | CANCER | 5 | Mint3/X11g-55KD (doublet) | 1 | O88888 | 9546 | 61 | 55 | 2 | + | 3.22 |
| 4303 | N25720 | CONTROL | 15 | Nm23 | 1 | P15531 | 4831 | 17 | 19 | 2 | + | 2.72 |
| 9702 | N41520 | CANCER | 28 | nNOS/NOS type I-172KD | 1 | P29476 | 4842 | 155 | 172 | 2 | + | 6.07 |
| 9704 | P49620 | CANCER | 31 | Paxillin-147KD | 1 | P49024 | 5829 | 68 | 147 | 2 | + | 2.51 |
| 9606 | P49620 | CANCER | 31 | Paxillin-75KD | 1 | P49024 | 5829 | 68 | 75 | 2 | − | 3.67 |
| 8502 | P56720 | CONTROL | 34 | PCNA | 1 | P12004 | 5111 | 36 | 28 | 2 | + | 2.24 |
| 8901 | P71720 | CONTROL | 34 | PDI | 1 | P05307 | 64714 | 55 | 55 | 2 | + | 2.00 |
| 4602 | P62220 | CANCER | 12 | PKR/p68 Kinase | 1 | P19525 | 5610 | 68 | 60 | 2 | + | 3.47 |

TABLE 7-continued

Low risk Subjects vs. Stage 0 Cancer Subjects
Level 1 - Changes greater than 2-fold from low quality signals

| SSP | Acc. No. | Type | Lane | Protein Name | Level | Swiss Prot ID | Locus | Predicted MW | MW | Signal | Change | FoldChange |
|---|---|---|---|---|---|---|---|---|---|---|---|---|
| 2401 | R56220 | CONTROL | 2 | Rac1 | 1 | P15154 | 207 | 21 | 24 | 2 | + | 2.86 |
| 9302 | | CONTROL | 37 | Rap2 | 1 | 0 | 0 | 21 | 20 | 2 | − | div/0 |
| 2702 | G12920 | CANCER | 9 | Ras-GAP | 1 | P20936 | 5921 | 120 | 128 | 2 | − | div/0 |
| 7902 | R68320 | CONTROL | 32 | Rb | 1 | P13405 | 19645 | 110 | 104 | 2 | + | 3.82 |
| 2901 | G16920 | CONTROL | 5 | Stat1 (N-terminus) | 1 | P42224 | 6772 | 91/84 | 86 | 2 | − | div/0 |
| 603 | T93820 | CANCER | 2 | TLS | 1 | P35637 | 2521 | 65 | 61 | 2 | − | 4.19 |

REFERENCES

The following references are cited in the preceding text:
1. Wulfkuhle, J. D.; Liotta, L. A.; Petricoin, E. F. Proteomic applications for the early detection of cancer. Nat Rev Can. 2003, 3(4), 267-75.
2. Pollard, T. The future of biomedical research, from the inventory of genes to understanding physiology and the molecular basis of disease. JAMA. 2002, 287(13), 1725-27.
3. Herrmann, P. C.; Liotta, L.; Petricoin, E. Cancer Proteomics: The state of the art. Dis Mkrs. 2001, 17, 49-57.
4. Srinivas, P. R.; Srivastava, S.; Hanash, S.; Wright, G. L. Proteomics in early detection of cancer. Clin Chem. 2001, 47(10), 1901-11.
5. Conrads, T. P.; Zhou, M.; Petricoin, E.; Liotta, L.; Veenstra, T. Cancer diagnosis using proteomic patterns. Expert Rev Mol. Diag. 2003, 3(4), 411-20.
6. Simpson, R. J.; Dorow, D. S. Cancer proteomics: From signaling networks to tumor markers. Trends Biotechnol. 2001, 19(10), S40-8.
7. Verma, M.; Wright, G. L.; Hanash, S. M.; Gopal-Srivastava, R.; Srivastava, S. Proteomic approaches within the NCI early detection research network for the discovery and identification of cancer biomarkers. Ann N Y Acad. Sci. 2001, 945, 103-15.
9. von Eggeling, F.; Junker, K.; Fiedle, W.; Wollscheid, V.; Durst, M.; Claussen, U.; Ernst, G. Mass spectrometry meets chip technology: a new proteomic tool in cancer research? Electrophoresis. 2001, 22(14), 2898-902.
10. Wong, D. T. Salivary diagnostics powered by nanotechnologies, proteomics and genomics. JADA. 2006, 137, 313-21.
11. Streckfus, C. F.; Bigler, L.; Dellinger, T. D.; Dai, X.; Kingman, A.; Thigpen, J. T. The presence of c-erbB-2, and CA 15-3 in saliva and serum among women with breast carcinoma: a preliminary study. Clin Cancer Res. 2000, 6(6), 2363-70.
12. Streckfus, C. F.; Bigler, L.; Tucci, M.; Thigpen, J. T.; The Presence of CA 15-3, c-erbB-2, EGFR, Cathepsin-D, and p53 in saliva among women with breast carcinoma. Cancer Invest. 2000, 18(2), 101-9.
13. Part VII Breast. In: Greene, F. L.; Page, D. L.; Fleming, I. D. et al. editors. AJCC Cancer Staging Handbook. 6th ed. New York: Springer-Verlag; 2001.
14. Birkhed, D.; Heintze, U. Salivary secretion rate, buffer capacity, and pH. In: Tenovuo, J. O., editor. Human Saliva: Clinical Chemistry and Microbiology—Volume 1. Boca Raton: CRC press; 1989.
15. Streckfus, C. F.; Bigler, L.; Dellinger, T. D.; Dai, X.; Cox, W. J.; McArthur, A.; Kingman, A.; Thigpen, J. T. Reliability assessment of soluble c-erbB-2 concentrations in the saliva of healthy women and men. Oral Surg Oral Med Oral Path. 2001, 91(2), 174-180.
16. Wilmarth, P. A.; Riviere, M. A.; Rustvold, D. L.; Lauten, J. D.; Madden, T. E.; David, L. L. Two dimensional liquid chromatography study of the human whole saliva proteome. J Prot Res. 2004, 3, 1017-23.
17. Gu, S.; Liu, Z.; Pan, S.; Jiang, Z.; Lu, H.; Amit, 0.; Bradbury, E. M.; Hu, C. A.; Chen, X. Global investigation of p53-induced apoptosis through quantitative proteomic profiling using comparative amino acid-coded tagging. Mol Cell Proteomics. 2004, 10, 998-1008.
18. Shevchenko, A.; Chernushevic, I.; Shevchenko, A.; Wilm, M.; Mann, M. "De novo" sequencing of peptides recovered from in-gel digested proteins by nanoelectrospray tandem mass spectrometry. Mol. Biotech. 2002, 20, 107-18.
19. Koomen, J. M.; Zhao, H.; Li, D.; Abbruzzese, J.; Baggerly, K.; Kobayashi, R. Diagnostic protein discovery using proteolytic peptide targeting and identification. Rapid Com Mass Spec. 2004, 18, 2537-48.
20. Ward, L. D.; Reid, G. E.; Moritz, R. L.; Simpson, R. J. Strategies for internal amino acid sequence analysis of proteins separated by polyacrylamide gel electrophoresis. J. Chroma. 1990, 519, 199-216.
21. Hu, S.; Xie, Y.; Ramachandran, P.; Loo, R. R. O.; Li, Y.; Loo, J. A.; Wong, D. T. Large scale identification of proteins in human saliva proteome by liquid chromatography/mass spectrometry and two-dimensional gel electrophoresis-mass spectrometry. Proteomics. 2005, 5, 1714-28.
22. Huang, C. M. Comparative proteomic analysis of human whole saliva. Arch Oral Biol. 2004, 49, 951-62.
23. Vitorino, R.; Lobo, M.; Ferrer-Correira, A. I.; Dubin, J. R.; Tome, K. B.; Domingues, P. M.; Amado, F. M. Identification of human whole saliva protein components using proteomics. Proteomics. 2004, 4, 1109-15.
24. Ghafouri, B.; Tagesson, C.; Lindahl, M. Mapping of proteins in human saliva using two-dimensional gel electrophoresis and peptide mass fingerprinting. Proteomics. 2003, 3(6), 1003-15.
25. Minafra, I. P.; Cancemi, P.; Fontana, S.; et al. Expanding the protein catalogue in the proteome reference map of human breast cancer cells. Proteomics. 2006, 6, 2609-25.
26. Wulfkuhle, J.; Sgroi, D.; Krutzsch, H.; et al. Proteomics of human breast carcinoma in situ. Cancer Res. 2002, 62, 6740-9.
27. Somiari, R.; Sullivan, A.; Russell, S.; et al. High-throughput proteomic analysis of infiltrating ductal carcinoma of the breast. Proteomics. 2003, 3, 1863-73.
28. Hudelist, G.; Singer, C.; Pischinger, K.; et al. Proteomic analysis in human breast cancer: Identification of a characteristic protein expression profile of malignant breast epithelium. Proteomics. 2006, 6, 1989-02.

29. Chamberry A.; Farina, A.; DiMaro, A.; et al. Proteomic analysis of MCF-7 cell lines expressing the Zinc finger or proline-rich domain of retinoblastoma-in reacting-zinc-finger protein. J Proteome Res. 2006, 5, 1176-85
30. Polanski, M.; Anderson NL. A list of candidate cancer biomarkers for targeted proteomics. Biomarker Insights. 2006, 2, 1-48.
31. Sokol, J. P.; Neil, J. R.; Schiemann, B. J.; Schiemann, W. P. The use of cystatin C to inhibit epithelial-mesenchymal transition and morphological transformation stimulated by transforming growth factor-β. Breast Can Res. 2005, 7, R844-R853.
32. Fernandez, C. A.; Li, Y.; Louis, G.; Yang, J.; Kutok, J.; Moses M. The matrix metalloproteinase-9/neutrophil gelatinase-associated lipocalin complex plays a role in breast tumor growth and is present in the urine of breast cancer patients. Clin Can Res. 2005, 11(15), 5390-5.
33. Josephy, P. D. The role of peroxidase-catalyzed activation of aromatic amines in breast cancer. Mutagenesis. 1996, 11(1), 3-7.
34. Huang, H. L.; Stasyk, T.; Morandell, S.; Dieplinger, H.; et al. Biomarker discovery in breast cancer serum using 2-D differential gel electrophoresis/MALDI-TOF/TOF and data validation by routine clinical assays. Electrophoresis. 2006, 27, 1641-1650.
35. Le, X. F.; Bedrosian, I.; Mao, W.; et al. Anti-HER2 antibody trastuzumab inhibits CDK2-mediated NPAT and histone H4 expression via the PI3K pathway. Cell Cycle. 2006, 5(15), 1654-61.
36. Sonora, C.; Mazal, D.; Berois, N.; et al. Immunohistochemical analysis of MUC5B apomucin expression in breast cancer and non-malignant breast tissues. J Histochem Cytochem. 2006, 54(3), 289-299.
37. Streckfus, C. F.; Bigler, L. R.; Dubinsky, W. P.; Bull, J. Salivary biomarkers for the detection of cancer. In. *Progress in Tumor Marker Research*, Swenson LI ed. Nova Scientific Publishing, Inc., New York, 2007.
38. Wick, M.; Ockner, D. M.; Mills, S.; Ritter, J.; Swanson, P. E. Homologous carcinomas of the breasts, skin, and salivary glands. A histologic and immunohistochemical comparison of ductal mammary carcinoma, ductal sweat gland carcinoma and salivary duct carcinoma. Am J Clin Pathol. 1998, 109, 75-84.
39. Kurachi, H.; Okamoto, S.; Oka, T. Evidence for the involvement of the submandibular gland epidermal growth factor in mouse mammary tumorigenesis. Proc Natl Acad Sci USA. 1985, 82, 5940-5943.
40. Kuerer, H. M.; Thompson, P. A.; Krishnamurthy, S.; Fritsche, H. A.; Marcy, S. M.; Babiera, G. V.; et al. High and differential expression of HER2/neu extracellular domain in bilateral ductal fluids from women with unilateral invasive breast cancer. Clin Canc Res. 2003, 9, 601-605.
41. Alexander, H.; Stegner, A. L.; Wagner-Mann, C.; Du Bois, G. C.; Alexander, S.; Sauter, E. R. Proteomic analysis to identify breast cancer biomarkers in nipple aspirate fluid. Clin Cancer Res. 2004, 10(22), 7500-10.
42. Charles F Streckfus, C. F.; Dubinsky W. P. Proteomic analysis of saliva for cancer diagnosis
Exp Rev Prot. 2007, 4(3), 329-332.
43. U.S. National Center for Research Resource, internet URL http://ncrr.pnl.gov/software/VennDiagramPlotter-.stm.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the representative description set out above, but is only limited by the claims which follow, that scope including all equivalents of the subject matter of the claims. The disclosures of all patents, patent applications, and publications cited herein are hereby incorporated herein by reference, to the extent that they provide exemplary, procedural, or other details supplementary to those set forth herein.

What is claimed is:

1. A method for determining an increased risk of developing a breast tumor in a test subject, the method comprising:
   (a) obtaining from the test subject a saliva sample and detecting at least a first protein biomarker in said sample, wherein said protein biomarker is selected from the group consisting of CAH6 (Carbonic anhydrase VI), K2C4 (Cytokeratin 4), CYTA (Cystatin A), FABP4 (Epid. Fatty acid binding prot.), IGHGI (Ig gamma-1 chain C region), TRFL (Lactoferrin), BPIL1 (Bact. Perm.-increasing prot.-1), CYTC (Cystatin C), HPT (Haptoglobin), PROF1 (Profilin-1), ZA2G (Zinc-alpha-2-glycoprotein), ENOA (Alpha enolase), IGHA2 (Ig alpha-2 chain C region), IL-1 ra (Interleukin-1 receptor anatagonist protein precursor), S10A7 (S100 calcium-binding protein A7), and SPLC2 (Short palate, lung and nasel epith Carc. assoc. protein 2), and wherein the protein biomarker is detected and characterized by transforming the first protein biomarker in the test sample by:
      (1) digesting and isotopic labeling said protein biomarker to form labeled-peptides,
      (2) performing liquid chromatography tandem mass spectrometry on said labeled peptides to generate fragment ions and fragmentation ion spectra,
      (3) inputting said fragmentation ion spectra into a computer; and
      (4) said computer performing a computer aided comparison of said fragmentation ion spectra to a protein sequence database, thereby identifying and characterizing the protein biomarkers from the saliva sample of the test subject; and wherein said protein biomarker is differentially expressed in breast tumor and tumor-free breast tissue;
   (a') measuring a concentration of said protein biomarker to provide a set of test data comprising a test concentration value of each protein biomarker in said saliva sample;
   (b) comparing said test concentration values from said test subject to a reference panel comprising
      (1) a mean concentration value of each protein biomarker in saliva from a group of breast tumor-free individuals (reference control group), and
      (2) a mean concentration value of each said protein biomarker in saliva from a group of individuals with ductal carcinoma in situ of the breast (DCIS) (reference DCIS group), or from a group of individuals with benign fibroadenoma of the breast (reference benign group), or from both the DCIS group and the benign group, wherein said reference panel is prepared by transforming salivary proteins in saliva from individuals of each said reference groups by (i) digesting and isotopic labeling said salivary proteins to form labeled-peptides, (ii) performing liquid chromatography tandem mass spectrometry on said labeled peptides to generate fragment ions and fragmentation ion spectra, (iii) inputting said fragmentation ion spectra into a computer; and (iv) said computer performing a computer aided comparison of said fragmentation ion spectra to a protein sequence database, thereby identifying and characterizing the protein biomarkers from each said group; and (c) determining from said comparison of said concentration values an increased risk of developing a breast tumor in the test subject by determining whether the test concentration values of each protein biomarker in the saliva sample from the test subject are significantly the same as or different from the mean concentration values for each said protein biomarker in the reference control group, the reference DCIS group or the reference benign group, wherein the concentration value of at least said first protein biomarker in said reference panel is significantly different in the saliva of said reference DCIS group and/or in the saliva of said reference benign group, relative to the respective concentration value of at least said first protein biomarker in the saliva of said reference control group, wherein the concentration values are significantly different at a level in the range of $p<0.05$ to $p<0.0001$.

2. The method of claim 1, wherein at least said first protein biomarker is selected from the group consisting of CAH6 (Carbonic anhydrase VI), K2C4 (Cytokeratin 4), CYTA (Cystatin A), FABP4 (Epid. Fatty acid binding prot.), IGHGI (Ig gamma-1 chain C region), TRFL (Lactoferrin), BPIL1 (Bact. Perm.-increasing prot.-1), CYTC (Cystatin C), HPT (Haptoglobin), PROF1 (Profilin-1), ZA2G (Zinc-alpha-2-glycoprotein),and, in (c), said determining comprises determining from said comparison an increased risk of developing DCIS in the test subject.

3. The method of claim 1, wherein at least said first protein biomarker is selected from the group consisting of ENOA (Alpha enolase), IGHA2 (Ig alpha-2 chain C region), IL-1ra (Interleukin-1 receptor antagonist protein precursor), S10A7 (S100 calcium-binding protein A7), SPLC2 (Short palate, lung and nasal epith Carc. assoc. protein 2), and, in (c), said determining comprises determining from said comparison an increased risk of developing fibroadenoma in the test subject.

4. The method of claim 1, wherein said isotopic labeling comprises differential isotopic labeling of salivary proteins of at least first and second saliva samples.

5. The method of claim 1, wherein, in (b), said comparing yields a comparison result in which the concentration value of at least said first protein biomarker is a significant change relative to the mean concentration value of the respective protein biomarker in the reference control group of the reference panel, wherein a significant change is determined by a p-value in the range of $<0.05$ to $<0.0001$.

6. The method of claim 1, wherein said saliva sample is a first saliva sample from said test subject, and, in (a'), the set of test data is a first set of test data, and the method further comprises:

(d) obtaining a second saliva sample from said subject subsequent to said first sample;

(e) measuring the concentration of at least said first protein biomarker in the second saliva sample, to provide a second set of test data comprising a second concentration value of each said protein biomarker in said saliva sample;

(f) comparing the second set of test data to said reference panel;

(g) determining from the result of said an increased risk of developing either DCIS or benign fibroadenoma of the breast in the test subject.

7. The method of claim 6, further comprising (h) comparing said second set of test data to said first set of test data to determine whether a difference in the concentration value of at least said first protein biomarker exists between said first and second sets of test data for said test subject.

8. The method of claim 7, wherein said first saliva sample is obtained prior to surgical removal of cancerous breast tissue from said subject.

9. The method of claim 8, wherein said test subject has received therapeutic treatment for breast cancer prior to obtaining said second saliva sample.

10. The method of claim 9 wherein, in (g), determining a comparative decrease in at least said first protein biomarker concentration in said second sample relative to said first sample indicates that the therapeutic treatment is effective.

11. A method of treating a human test subject suffering from a breast tumor, comprising determining whether the subject has an increased risk of developing a breast tumor according to claim 1, and exposing the subject to a treatment that ameliorates or reverses the symptoms of a breast tumor on the basis that the subject tests positive for the said protein markers indicative of either DCIS or benign fibroadenoma as determined by said comparison of step (c).

12. A method of diagnosing the likelihood of the presence or occurrence of a breast tumor in a test subject, the method comprising:

1) producing a reference panel comprised of at least one protein biomarker, wherein said biomarker is identified from saliva samples of individuals that are tumor free (reference control group); diagnosed with DCIS (ductal carcinoma in situ of the breast (reference DCIS group)); or diagnosed with benign fibroadenoma (reference benign group); wherein said biomarkers are identified and characterized by:

(a) digesting said biomarkers to form peptides, and isotopic labeling said peptides to form isotopically labeled-peptides;

(b) performing liquid chromatography tandem mass spectrometry on said isotopically labeled-peptides to generate fragmentation ions and fragment ion data; and (c) inputting said fragmentation ion data into a computer, and transforming said fragmentation ion data into protein sequences; and (d) comparing said sequences to protein databases to identify said protein biomarkers, wherein said identified biomarkers are selected from the group consisting of CAH6 (Carbonic anhydrase VI), K2C4 (Cytokeratin 4), CYTA (Cystatin A), FABP4 (Epid. Fatty acid binding prot.), IGHGI (Ig gamma-1 chain C region), TRFL (Lactoferrin), BPIL1 (Bact. Perm.-increasing prot.-1), CYTC (Cystatin C), HPT (Haptoglobin), PROF1 (Profilin-1), ZA2G (Zinc-alpha-2-glycoprotein), ENOA (Alpha enolase), IGHA2 (Ig alpha-2 chain C region), IL-1 ra (Interleukin-1 receptor antagonist protein precursor), S10A7 (S100 calcium-binding protein A7), and SPLC2 (Short palate, lung and nasel epith Carc. assoc. protein 2);

2) electronically storing by a computer mean concentration values for said protein biomarkers of said reference panel on a non-transitory computer readable storage device;

3) retrieving said mean concentrations of said protein biomarkers from said computer readable storage device; comparing by the computer said mean concentrations of said protein biomarkers to mean concentrations of test protein biomarkers, wherein said test protein biomarkers are comprised of proteins from a saliva sample of a test subject; and wherein the test protein biomarkers of the test subject are detected and characterized by transforming the test protein biomarkers in the test sample by: (a) digesting and isotopic labeling said test protein biomarkers to form labeled-peptides, (b) performing liquid chromatography tandem mass spectrometry on said labeled peptides to generate fragment ions and fragmentation ion data, (c) inputting said fragmentation ion data into a computer; and (d) said computer performing a computer aided comparison of said fragmentation ion spectra to a protein sequence database, thereby identifying and characterizing the test protein biomarkers from the saliva sample of the test subject;

4) determining by said computer from said comparing of said mean concentrations of said protein biomarkers in the reference panel to mean concentrations of said test protein biomarkers from said test subject, a diagnosis of likelihood of the presence or occurrence of a breast tumor in the test subject by determining whether the test concentration values for each protein biomarker in the saliva sample from the test subject are significantly the same as or different from the mean concentration values for each said protein biomarker: in the reference control group, the reference DCIS group, or the reference benign group, wherein the mean concentration value of at least a first protein biomarker in said reference panel is significantly different in the saliva of said reference DCIS group and/or in the saliva of said reference benign group, relative to the respective mean concentration value of at least said first protein biomarker in the saliva of said reference control group, wherein the concentration values are significantly different at a level in the range of $p<0.05$ to $p<0.0001$.

13. A method of treating a test subject suffering from a breast tumor, comprising:
    (1) (a) obtaining from the test subject a saliva sample and detecting at least a first protein biomarker in said sample, wherein said protein biomarker is selected from the group consisting of CAH6 (Carbonic anhydrase VI), K2C4 (Cytokeratin 4), CYTA (Cystatin A), FABP4 (Epid. Fatty acid binding prot.), IGHGI (Ig gamma-1 chain C region), TRFL (Lactoferrin), BPIL1 (Bact. Perm.-increasing prot.-1), CYTC (Cystatin C), HPT (Haptoglobin), PROF1 (Profilin-1), ZA2G (Zinc-alpha-2-glycoprotein), ENOA (Alpha enolase), IGHA2 (Ig alpha-2 chain C region), IL-1ra (Interleukin-1 receptor anatagonist protein precursor), S10A7 (S100 calcium-binding protein A7), and SPLC2 (Short palate, lung and nasel epith Carc. assoc. protein 2), and wherein the protein biomarker is detected and characterized by transforming the first protein biomarker in the test sample by: (a) digesting and isotopic labeling said protein biomarker to form labeled-peptides, (b) performing liquid chromatography tandem mass spectrometry on said labeled peptides to generate fragment ions and fragmentation ion spectra, (c) inputting said fragmentation ion spectra into a computer; and (d) said computer performing a computer aided comparison of said fragmentation ion spectra to a protein sequence database, thereby identifying and characterizing the protein biomarkers from the saliva sample of the test subject; and wherein said protein biomarker is differentially expressed in breast tumor and tumor-free breast tissue;

(a') measuring a concentration of said protein biomarker to provide a set of test data comprising a test concentration value of each protein biomarker in said saliva sample;
    (b) comparing said test concentration values from said test subject to a reference panel comprising:
        (1) a mean concentration value of each protein biomarker in saliva from a group of breast tumor-free individuals (reference control group), and
        (2) a mean concentration value of each said protein biomarker in saliva from a group of individuals with ductal carcinoma in situ of the breast (DCIS) (reference DCIS group), or from a group of individuals with benign fibroadenoma of the breast (reference benign group), or from both the DCIS group and the benign group, wherein said reference panel is prepared by transforming salivary proteins in saliva from individuals of each said reference groups by (i) digesting and isotopic labeling said salivary proteins to form labeled-peptides, (ii) performing liquid chromatography tandem mass spectrometry on said labeled peptides to generate fragment ions and fragmentation ion spectra, (ii) inputting said fragmentation ion spectra into a computer; and (iv) said computer performing a computer aided comparison of said fragmentation ion spectra to a protein sequence database, thereby identifying and characterizing the protein biomarkers from each said group; and
    (c) determining from said comparison of said concentration values a diagnosis of the likelihood of the presence or occurrence of a breast tumor in the test subject by determining whether the test concentration values of each protein biomarker in the saliva sample from the test subject are significantly the same as or different from the mean concentration values for each said protein biomarker in the reference control group, the reference DCIS group or the reference benign group, wherein the concentration value of at least said first protein biomarker in said reference panel is significantly different in the saliva of said reference DCIS group and/or in the saliva of said reference benign group, relative to the respective concentration value of at least said first protein biomarker in the saliva of said reference control group, wherein the concentration values are significantly different at a level in the range of $p<0.05$ to $p<0.0001$; and
    (2) exposing the test subject to a treatment that ameliorates or reverses the symptoms of a breast tumor based on the diagnosis of 1(c).

\* \* \* \* \*